United States Patent
Hatori et al.

(10) Patent No.: US 8,367,614 B2
(45) Date of Patent: Feb. 5, 2013

(54) RHEUMATOID ARTHRITIS-PREVENTIVE AGENT FOR ORAL INTAKE

(75) Inventors: Michio Hatori, Sagamihara-shi, Kanagawa (JP); Kohji Ohki, Sagamihara-shi, Kanagawa (JP); Naomi Hashimura, Sagamihara-shi, Kanagawa (JP); Tatsuhiko Hirota, Sagamihara-shi, Kanagawa (JP); Kazuhito Ohsawa, Sagamihara-shi, Kanagawa (JP)

(73) Assignee: Calpis Co., Ltd, Tokyo (JP)

( * ) Notice: Subject to any disclaimer, the term of this patent is extended or adjusted under 35 U.S.C. 154(b) by 0 days.

(21) Appl. No.: 13/161,098

(22) Filed: Jun. 15, 2011

(65) Prior Publication Data

US 2011/0251129 A1    Oct. 13, 2011

Related U.S. Application Data

(63) Continuation of application No. 12/278,880, filed as application No. PCT/JP2007/052368 on Feb. 9, 2007, now abandoned.

(30) Foreign Application Priority Data

Feb. 9, 2006  (JP) ................... 2006-032826

(51) Int. Cl.
*A61K 38/00*  (2006.01)
*A61P 19/02*  (2006.01)
*A61P 29/00*  (2006.01)

(52) U.S. Cl. ..................................... 514/16.6

(58) Field of Classification Search ............... None
See application file for complete search history.

(56) References Cited

U.S. PATENT DOCUMENTS

| | | | |
|---|---|---|---|
| 5,314,873 A | 5/1994 | Tomita et al. | |
| 6,994,987 B1 | 2/2006 | Yamamoto et al. | |
| 2005/0180966 A1 | 8/2005 | Hirschman | |
| 2005/0256057 A1 | 11/2005 | Edens et al. | |
| 2007/0299014 A1 | 12/2007 | Yamamoto et al. | |
| 2011/0082281 A1* | 4/2011 | Yamamoto et al. | 530/331 |

FOREIGN PATENT DOCUMENTS

| | | |
|---|---|---|
| JP | 09-059297 A | 3/1997 |
| JP | 2001-136995 A | 5/2001 |
| JP | 2002-255847 A | 9/2002 |
| JP | 2003-137807 A | 5/2003 |
| JP | 2004-155751 A | 6/2004 |
| JP | 2005-528110 A | 9/2005 |
| WO | 03-093308 A1 | 11/2003 |
| WO | 2004/098309 A1 | 11/2004 |
| WO | 2005/012542 A1 | 2/2005 |

OTHER PUBLICATIONS

Hatori et al., "Japan Society for Bioscience, Biotechnology, and Agrochemistry 2006 Nen Taikai Ippan Koen Topics (1)," The Food Industry, 2006, pp. 71-72, vol. 49, No. 16.

Hatori et al., "Adjuvant Kansetsuen Rat ni Okeru Casein Koso Bunkaibutsu no Kansetsuen Yobo Koka," Japan Society for Bioscience, Biotechnology, and Agrochemistry 2006 Nendo Taikai Koen Yoshishu, 2006, p. 43, 2J10p01.

Yamamoto et al., Antihypertensince Peptides Derived from Milk Proteins; Nahrung 43, Nr. 3, S. pp. 159-164, 1999.

Hatori et al., Effects of a Casein Hydrolysate Prepared from *Aspergillus oryzae* Protease on Adjuvant Arthritis in Rates; Biotechnol. Biochem. 72(8), pp. 1983-1991; 2008.

* cited by examiner

*Primary Examiner* — Marcela M Cordero Garcia
(74) *Attorney, Agent, or Firm* — Sughrue Mion, PLLC

(57) ABSTRACT

There is provided a rheumatoid arthritis inhibitor for oral intake that has an inhibitory effect on rheumatoid arthritis and is excellent in safety. The rheumatoid arthritis inhibitor for oral intake of the present invention contains, as an active component, a casein hydrolysate containing free amino acids and peptides obtained by hydrolyzing animal milk casein to have an average chain length of not longer than 2.1 in terms of the number of amino acid residues, or a mixture of free amino acids and peptides contained in the hydrolysate.

6 Claims, 1 Drawing Sheet

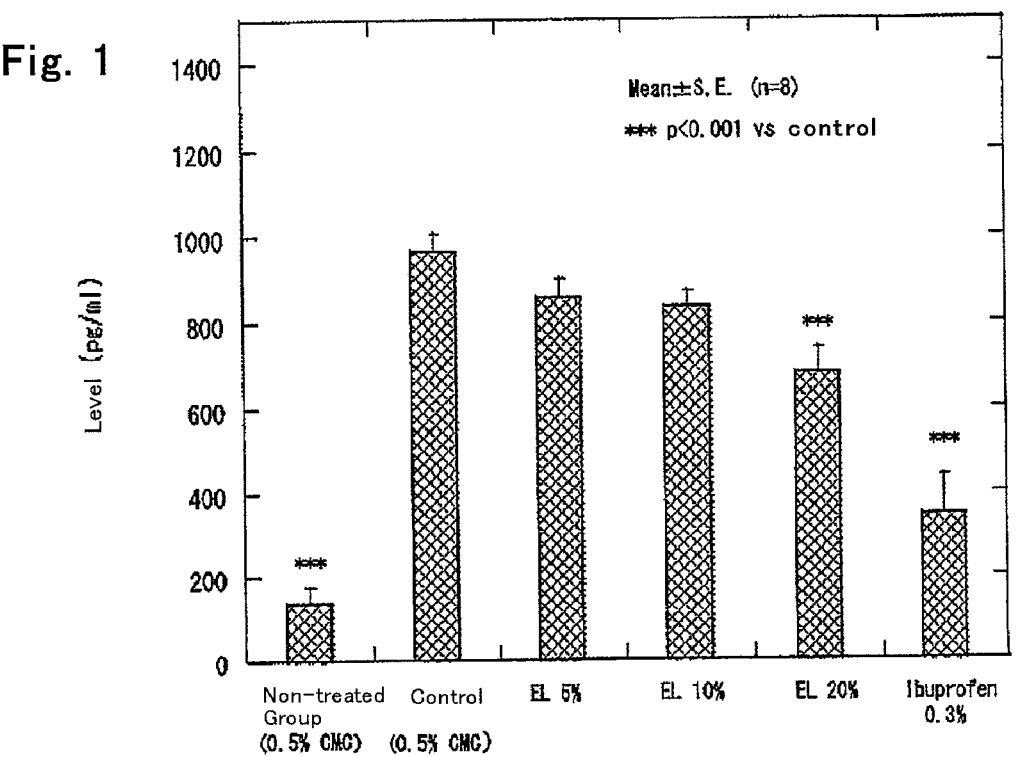
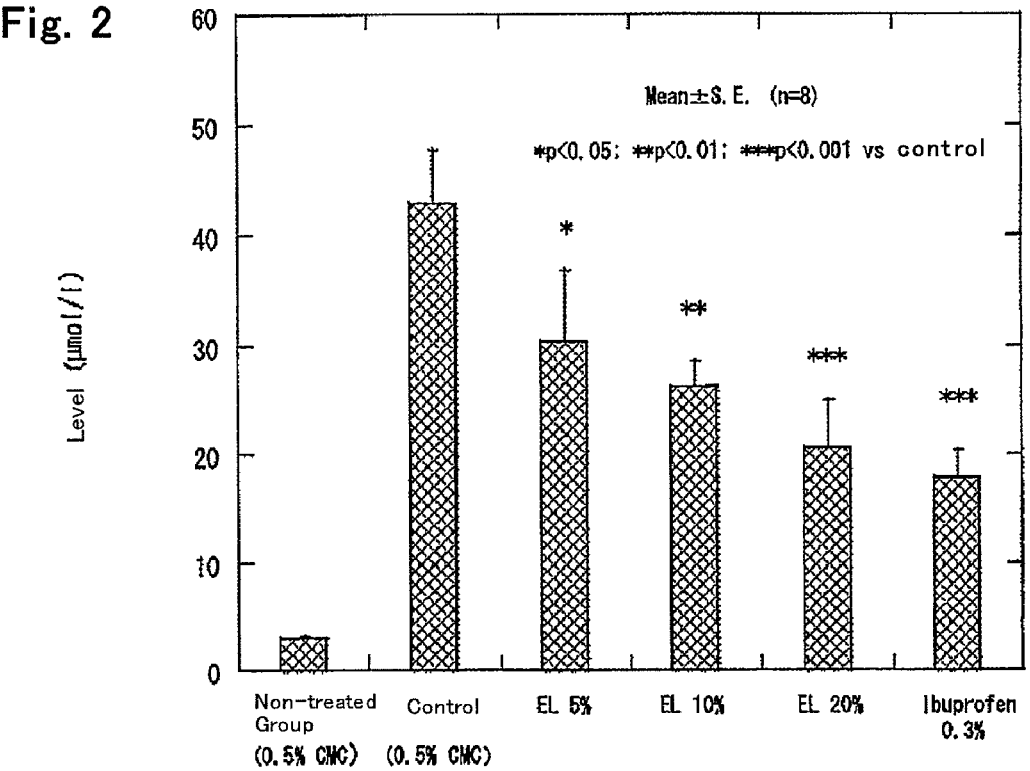

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial sequence
<220> FEATURE:
<223> OTHER INFORMATION: Description of Artificial Sequence: sequence
      from animal milk casein
<220> FEATURE:
<221> NAME/KEY: MOD_RES
<222> LOCATION: (1)..(1)
<223> OTHER INFORMATION: variable amino acid
```

```
<220> FEATURE:
<221> NAME/KEY: MOD_RES
<222> LOCATION: (4)..(4)
<223> OTHER INFORMATION: variable amino acid

<400> SEQUENCE: 1

Xaa Pro Pro Xaa
1
```

RHEUMATOID ARTHRITIS-PREVENTIVE AGENT FOR ORAL INTAKE

CROSS-REFERENCE TO RELATED APPLICATIONS

This application is a continuation of U.S. patent application Ser. No. 12/278,880, filed on Jan. 27, 2009 (abandoned), which is a §371 National Stage application of International Application No. PCT/JP2007/052368, filed Feb. 9, 2007, which claims priority from Japanese Patent Application No. 2006-032826, filed Feb. 9, 2006 in the Japanese Patent Office, the disclosures of which are incorporated herein in their entireties by reference.

FIELD OF ART

The present invention relates to a rheumatoid arthritis inhibitor for oral intake that contains, as an active component, a particular hydrolysate of animal milk casein having an inhibitory effect on rheumatoid arthritis, such as chronic rheumatoid arthritis, through oral intake, as well as functional food expected to have such an inhibitory effect.

BACKGROUND ART

Chronic rheumatoid arthritis (sometimes abbreviated as RA hereinbelow) is an autoimmune disease, wherein inflammation is produced chronically at joints to cause swelling or degeneration due to a cause unknown to date.

It is believed that the inflammation in RA is associated with prostaglandin E (PGE), prostacyclin (PGI), histamine, or kinin such as bradykinin, so that anti-inflammatory agents, typically NSAIDs (nonsteroidal anti-inflammatory drugs), are often prescribed as a first treatment. When such anti-inflammatory agents do not take effect, then antirheumatic drugs are prescribed, such as immunosuppressants that suppress the overall immune function by suppressing inflammatory cytokines, such as TNF-α, interleukin-1 (IL-1), or IL-6, which are involved in immunomodulation via T-lymphocytes or B-lymphocytes, or immunomodulators that suppress only the abnormal immune function relating to RA. Recently, such antirheumatic drugs may sometimes be prescribed even in the initial stage of treatment.

However, antirheumatic drugs, such as the conventional immunosuppressants or immunomodulators, have side effects of some kind, so that prescription for such drugs should be restricted to some extent. In order to suppress the side effects as much as possible, a molecular biological approach which is targeted only to the molecules that exaggerate RA, has recently been made. Biopharmaceuticals have also been under development, utilizing, for example, anti-TNF-α monoclonal antibodies, soluble TNF-α receptor (sT-NFR) fusion protein, IL-1 receptor antagonists, or IL-6 receptor antibodies.

On the other hand, there have conventionally been identified various physiological functions of milk components and digestion products thereof. For example, Patent Publication 1 discloses that certain enzymatic digestion products of certain milk protein have a TNF-α or IL-6 inhibitory effect, and may mitigate systemic inflammatory response syndrome or inflammatory responses. Patent Publication 2 discloses that a casein hydrolysate containing free amino acids and peptides which has been obtained by hydrolyzing animal milk casein to have an average chain length of not longer than 2.1 in terms of the number of amino acid residues, has an angiotensin I converting enzyme inhibitory activity and a hypotensive effect.

However, it is not known to date that milk components or digestion products thereof, which are known as a food material and have sufficiently assured safety, have a RA inhibitory effect.

Patent Publication 1: JP-2004-155751-A
Patent Publication 2: WO-2005-102542-A

SUMMARY OF THE INVENTION

It is an object of the present invention to provide a rheumatoid arthritis inhibitor for oral intake that has an inhibitory effect on arthritis associated with rheumatoid arthritis, gives little concerns for side effects, and is excellent in safety.

It is another object of the present invention to provide functional food, such as health foods or foods for specified health uses, that may be subjected to daily and regular intake, is excellent in safety, and is expected to have an inhibitory effect on arthritis associated with rheumatoid arthritis.

According to the present invention, there is provided a rheumatoid arthritis inhibitor for oral intake comprising, as an active component, a casein hydrolysate comprising free amino acids and peptides obtained by hydrolyzing animal milk casein to have an average chain length of not longer than 2.1 in terms of the number of amino acid residues, or a mixture of free amino acids and peptides contained in said hydrolysate.

According to the present invention, there is also provided functional food comprising, as an active component, a casein hydrolysate comprising free amino acids and peptides obtained by hydrolyzing animal milk casein to have an average chain length of not longer than 2.1 in terms of the number of amino acid residues, or a mixture of free amino acids and peptides contained in said hydrolysate, and having an inhibitory effect on rheumatoid arthritis.

According to the present invention, there is further provided use of a casein hydrolysate comprising free amino acids and peptides obtained by hydrolyzing animal milk casein to have an average chain length of not longer than 2.1 in terms of the number of amino acid residues, or use of a mixture of free amino acids and peptides contained in said hydrolysate, in the manufacture of a rheumatoid arthritis inhibitor for oral intake.

According to the present invention, there is also provided a method for inhibiting rheumatoid arthritis comprising the step of orally administering an effective amount of a casein hydrolysate comprising free amino acids and peptides obtained by hydrolyzing animal milk casein to have an average chain length of not longer than 2.1 in terms of the number of amino acid residues, or a mixture of free amino acids and peptides contained in said hydrolysate.

Containing, as an active component, the particular casein hydrolysate or a mixture of free amino acids and peptides contained in the casein hydrolysate, which are known as a food material, the rheumatoid arthritis inhibitor for oral intake and the functional food according to the present invention are excellent in safety, and may be expected to have an inhibitory effect on arthritis and the like as sociated with rheumatoid arthritis. In particular, when the active component is made into an agent in the form of powders of tablets and added to functional food or the like, the resulting product may be subjected to daily and regular intake.

BRIEF DESCRIPTION OF THE DRAWINGS

FIG. 1 is a graph showing the results of the plasma $PGE_2$ measurement in evaluation against adjuvant arthritis conducted in Example 2.

FIG. 2 is a graph showing the results of the plasma NO measurement in evaluation against adjuvant arthritis conducted in Example 2.

PREFERRED EMBODIMENTS OF THE INVENTION

The present invention will now be explained in detail.

The rheumatoid arthritis inhibitor and the functional food according to the present invention contain, as an active component, a casein hydrolysate containing free amino acids and peptides obtained by hydrolyzing animal milk casein to have an average chain length of not longer than 2.1 in terms of the number of amino acid residues, preferably in an amount of not less than 80 wt %, more preferably 80 to 90 wt % of the casein hydrolysate, or a mixture of free amino acids and peptides contained in the hydrolysate. It is particularly preferred that the peptides include a particular ratio of peptides resistant to in vivo digestion consisting of dipeptides of the sequence Xaa-Pro and tripeptides of the sequence Xaa-Pro-Pro. The peptides may be in the form of peptide salts.

As used herein, the average chain length may be expressed as a ratio of the total number of moles of the peptides and the free amino acids generated by hydrolysis of animal milk casein with respect to the number of moles of all the amino acids in the acid hydrolysate of casein of the same weight. Here, the acid hydrolysate of casein is obtained by digesting casein protein into single amino acids.

The average chain length may be determined, for example, by evaluating the molar concentrations of the amino groups in the hydrolysate by the OPA method using an OPA (o-phthalaldehyde) reagent, which colors by reaction with amino groups, and expressed as:

Average chain length=(number of moles of amino groups in casein acid hydrolysate)/(number of moles of amino groups in casein enzymatic hydrolysate).

As used herein, the peptides resistant to in vivo digestion mean dipeptides Xaa-Pro and tripeptides Xaa-Pro-Pro having Pro at the carboxyl terminal, which have high digestion resistance against in vivo peptidases when absorbed intestinally in living organism.

According to the present invention, the average chain length of the hydrolysate obtained by hydrolyzing animal milk casein is not longer than 2.1, preferably 1.1 to 2.1, more preferably 1.3 to 2.1, in terms of the number of amino acid residues. With the average chain length of longer than 2.1, the contents of the desired dipeptides and tripeptides as well as the free amino acids are low, and thus the content of the desired in vivo absorbable peptides, moreover the peptides resistant to in vivo digestion, is low, in which case the desired effect may not be obtained.

The content of the dipeptides having the sequence Xaa-Pro in the casein hydrolysate is usually not lower than 5 wt %, preferably 5 to 25 wt % of the total amount of the peptides and the free amino acids in the hydrolysate. At less than 5 wt %, the desired effect may be lowered.

The content of the tripeptides having the sequence Xaa-Pro-Pro in the casein hydrolysate is usually not lower than 1 wt %, preferably 1 to 5 wt % of the total amount of the peptides and the free amino acids in the hydrolysate. At less than 1 wt %, the desired effect may be lowered.

In the peptides in the casein hydrolysate, Xaa in the dipeptides having the sequence Xaa-Pro and in the tripeptides having the sequence Xaa-Pro-Pro, may be any amino acid. For example, the dipeptides having the sequence Xaa-Pro may be Ile-Pro, Glu-Pro, Arg-Pro, Gln-Pro, Met-Pro, or Tyr-Pro, and the tripeptides having the sequence Xaa-Pro-Pro may be Ser-Pro-Pro, Ile-Pro-Pro, or Val-Pro-Pro. The casein hydrolysate may preferably be those containing at least one or all of the dipeptides and tripeptides listed above.

The casein hydrolysate contains free amino acids in addition to the peptides. The content of the free amino acids is usually 35 to 50 wt %, preferably 40 to 45 wt % of the total amount of the peptides and the free amino acids in the hydrolysate.

The casein hydrolysate may optionally contain, in addition to the peptides and the free amino acids, for example, lipid, ash, carbohydrate, dietary fibers, and water, which are usually contained in commercially available animal milk casein, in the amount of about 10 to 20 wt %. Some or all of these ingredients may be removed as desired.

The casein hydrolysate may be prepared, for example, by hydrolyzing animal milk casein to have an average chain length of not longer than 2.1 with a group of enzymes capable of digesting animal milk casein into a hydrolysate having an average chain length of not longer than 2.1 in terms of the number of amino acid residues.

The animal milk casein is a protein having a high Pro content and confirmed safety for use in food and the like, and may be, for example, casein from cow's milk, horse's milk, goat's milk, and sheep's milk, with cow's milk casein being particularly preferred.

The casein concentration in hydrolyzing animal milk casein is not particularly limited, and may preferably be 3 to 19 wt % for efficient production of the hydrolysate.

The group of enzymes may be any group of enzymes wherein enzymes capable of digesting animal milk casein into a hydrolysate having an average chain length of not longer than 2.1 in terms of the number of amino acid residues are suitably selected and combined. For example, a group of enzymes (X) containing peptidases capable of cleaving the peptide bond Pro-Xaa in the carboxyl terminal of Xaa-Pro-Xaa or Xaa-Pro-Pro-Xaa (SEQ ID NO: 1), may preferably be used.

The group of enzymes (X) may preferably contain serine proteinases having serine at the active center, or metalloproteinases having a metal at the active center. The metalloproteinases may be neutral protease I, neutral protease II, or leucine amino peptidase. With at least one of these metalloproteinases, the objective hydrolysate may be obtained efficiently in a short time, and even in a one-step reaction, thus being preferred. The peptidases capable of cleaving the peptide bond Pro-Xaa may preferably be enzymes having isoelectric points in the acid region.

The group of enzymes or the group of enzymes (X) may be, for example, a group of enzymes derived from *Aspergillus*, such as *Aspergillus oryzae*. Such a group of enzymes may be those obtained by culturing cell body in an appropriate medium, and water-extracting the produced enzymes. A group of enzymes derived from *Aspergillus oryzae* having isoelectric points in the acid region are particularly preferred.

The group of enzymes derived from *Aspergillus oryzae* may be a commercial product, such as SUMIZYME FP, LP, or MP (all registered trademarks, manufactured by SHIN NIHON CHEMICAL CO., LTD.), UMAMIZYME (registered trademark, manufactured by AMANO ENZYME, INC.), Sternzyme B11024 and PROHIDROXY AMPL (both trade names, manufactured by HIGUCHI INC.), ORIENTASE ONS (registered trademark, manufactured by HANKYU BIOINDUSTRY CO.), and DENAZYME AP (registered trademark, manufactured by NAGASE SEIKAGAKU), with SUMIZYME FP (registered trademark, manufactured by SHIN NIHON CHEMICAL CO., LTD.) being particularly preferred.

Such commercially available group of enzymes usually have specific optimum conditions. The conditions, such as the amount of enzymes used and the reaction time, may suitably be adjusted depending on the group of enzymes used so that the objective casein hydrolysate may be obtained.

For the hydrolysis, the group of enzymes may be, for example, added to an aqueous solution of animal milk casein at a group of enzymes/animal milk casein ratio of not lower than 1/1000, preferably 1/1000 to 1/10, more preferably 1/100 to 1/10, most preferably 1/40 to 1/10, by weight.

The reaction conditions may suitably be selected depending on the group of enzymes used so that the objective casein hydrolysate is obtained. The reaction may usually be effected at 25 to 60° C., preferably 45 to 55° C., at pH 3 to 10, preferably 5 to 9, more preferably 5 to 8. The enzyme reaction time is usually 2 to 48 hours, preferably 7 to 15 hours.

The enzyme reaction may be terminated by inactivating the enzymes. Usually, the enzymes are inactivated at 60 to 110° C. to terminate the reaction.

After the termination of the enzyme reaction, the resulting precipitate may preferably be removed by centrifugation or through various filters, as desired.

Further, the obtained hydrolysate may be subjected to removal of peptides having bitter taste or odor, which may be effected using activated carbon, a hydrophobic resin, or the like. For example, 1 to 20 wt % of activated carbon with respect to the amount of casein used may be added to the hydrolysate, and reacted for 1 to 10 hours to remove such bitter and odorous components. The activated carbon used may be removed by a conventional method, such as centrifugation or membrane filtration.

The reaction liquid containing the casein hydrolysate may be added as it is to liquid products such as beverages to manufacture functional food. For improving the versatility of the casein hydrolysate, the reaction liquid may preferably be concentrated and dried into powders to produce a functionality imparting agent which imparts an inhibitory effect on rheumatoid arthritis.

Such powders may optionally be mixed with various auxiliary additives for improving the nutritional balance or flavor. Examples of such auxiliary additives may include various carbohydrates, lipids, vitamins, minerals, sweeteners, flavoring agents, pigments, and texture improvers.

The effective dose of the rheumatoid arthritis inhibitor according to the present invention is usually 0.04 to 100 g, preferably about 0.2 to 20 g per day for human in terms of dried casein hydrolysate or dried peptide and free amino acids contained in the casein hydrolysate. The dose may be administered in several divided doses per day.

The dosing period for the rheumatoid arthritis inhibitor may be adjusted for the symptoms and the like, and is usually 1 to 365 days. Regular intake is preferred.

The route of administration of the rheumatoid arthritis inhibitor according to the present invention is oral, and the inhibitor may be in the form of a formulation for oral administration, such as tablets, pills, hard capsules, soft capsules, microcapsules, powders, granules, and liquids.

The formulation may be made, for example, with a carrier, adjuvant, excipient, auxiliary excipient, antiseptic, stabilizer, binder, pH regulator, buffer, thickener, gelatinizer, preservative, anti-oxidant, or the like, as desired, which are acceptable for pharmaceutical use, and manufactured in a unit dose form that is required in generally approved formulation.

The functional food according to the present invention may be produced as health foods or foods for specified health uses claiming or advertising the effect of inhibiting rheumatoid arthritis.

Taking into account the fact that the present functional food may be taken regularly, and daily over a prolonged period of time, the intake of the present functional food for obtaining the inhibitory effect on rheumatoid arthritis is usually 0.04 to 100 g, preferably about 0.2 to 20 g per day for human in terms of dried casein hydrolysate or dried mixture of peptides and free amino acids contained in the casein hydrolysate. The single intake of the functional food may be less than the above amount, depending on the number of intakes per day.

The period for taking the functional food of the present invention is not particularly limited, and it is preferred to take it for a prolonged period of time. In order to obtain the effect discussed above, it is preferred to take the functional food regularly for usually one day or longer, particularly about 20 days to 12 months.

The functional food according to the present invention may optionally contain, in addition to the active component casein hydrolysate or peptides and free amino acids contained in the casein hydrolysate, additives, such as other components used in food and beverages, for example, sugars, proteins, lipids, vitamins, minerals, flavoring agents, and mixtures thereof.

The functional food of the present invention may be made in any form, such as solid, gel, or liquid, by adding the casein hydrolysate or the peptides and free amino acids contained in the casein hydrolysate as it is or in powder or granular form to various food and beverages. For example, the present functional food may be in the form of beverages, yogurt, fluid diet, jelly, candies, retort pouch food, tablet candies, cookies, sponge cakes, breads, biscuits, or chocolates.

EXAMPLES

The present invention will now be explained in more detail with reference to Examples, Analytic Examples, and Comparative Examples, which are illustrative only and do not limit the present invention.

Production Example 1

1 g of casein derived from cow's milk (manufactured by NIPPON NZMP (Japan) LTD.) was added to 99 g of distilled water adjusted to about 80° C., and the resulting mixture was thoroughly stirred. The pH of the mixture was adjusted to 7.0 with 1N sodium hydroxide solution (manufactured by WAKO PURE CHEMICAL INDUSTRIES, LTD.), and the temperature was adjusted to 20° C., to prepare a substrate solution.

To this substrate solution, a commercially available enzyme (Sumizyme FP, registered trademark, manufactured by SHIN NIHON CHEMICAL CO., LTD.), which is derived from *Aspergillus oryzae* and contains at least metal protease, serine protease, neutral protease I, neutral protease II, and leucine amino peptidase, was added at the enzyme/casein ratio of 1/25 by weight, and the resulting mixture was reacted at 50° C. for 14 hours. Then the reaction product was autoclaved at 110° C. for 10 minutes to inactivate the enzyme, thereby obtaining a solution of enzymatic hydrolysate of casein. The solution of enzymatic hydrolysate was dried in a spray dryer to prepare a powder.

The resulting powder was analyzed for composition. The protein content was determined by the Kjeldahl method, and the amino acid content was determined with an amino acid analyzer. The peptide content was calculated by subtracting the amino acid content from the protein content. Further, the lipid content was determined by the acid hydrolysis method, the ash content by the direct asking method, and the moisture content by the air oven method. The hydrocarbon content was taken as the remainder after subtracting the contents of these components from 100%. As a result, it was determined that the amino acid content was 35.8 wt %, the peptide content 45.7 wt %, the moisture content 6.6 wt %, the lipid content 0.2 wt %, the ash content 4.1 wt %, and the hydrocarbon content 7.6 wt %.

<Determination of Average Chain Length>

The average chain length of the amino acids and the peptides contained in the obtained powder was determined by measuring the number of moles using an OPA reagent, which reacts with amino groups of the free amino acids and the peptides in the powder, similarly measuring the number of moles of a casein acid hydrolysate, and evaluating the ratio of these two.

40 mg of o-phthalaldehyde (guaranteed reagent for fluorescence analysis, manufactured by NACALAI TESQUE, INC.) was dissolved in 1 ml of methanol, and 100 µl of β-mercaptoethanol was added. The o-phthalaldehyde solution was diluted to 25 ml with 25 ml of a 100 mM sodium tetraborate solution previously mixed with 2.5 ml of 20% dodecyl sodium sulfate, and further to 50 ml with distilled water, to prepare an OPA reagent.

The powder sample of 1% casein enzymatic hydrolysate obtained by reaction with the enzyme was dissolved in an appropriate solvent at an appropriate concentration, and centrifuged at 15000 rpm for 10 minutes. 50 µl of the supernatant was taken out. Then 1 ml of the OPA reagent prepared above was added, thoroughly stirred, and left at a room temperature for 5 minutes. The absorbance at 340 nm was measured using an absorptiometer (trade name Ubest-35, manufactured by JASCO CORPORATION).

A 1% casein acid hydrolysate was prepared, properly diluted, and subjected to the same measurement to obtain a calibration curve, from which the relationship between absorbance and molar concentration was determined. The average chain length was calculated in accordance with the following formula and determined to be 1.4.

Average chain length=(molar concentration of 1% casein acid hydrolysate)/(molar concentration of each sample 1% casein enzymatic hydrolysate)

<Determination of Amino Acids Constituting Peptides>

The powder prepared above was dissolved in a suitable amount of distilled water, and analyzed in an automated protein sequencer (trade name PPSQ-10, manufactured by SHIMADZU CORPORATION) for amino acid sequence from the N-terminal. The results are shown in Table 1. Incidentally, the automated protein sequencer does not detect free amino acids.

The total amount of the amino acids at residue 5 was 120 pmol, and the total amount of the amino acids at residue 6 was 100 pmol. From these results, it was found that most of the peptides contained in the powder were di- and tripeptides. Further, the percentage of the peptides having Pro at residue 2 was 49.5%, which was remarkably high, and the percentage of the peptides having Pro at residue 3 was also as high as 29.8%.

Consequently, it is estimated that the content of Xaa-Pro or Xaa-Pro-Pro in the powder is high, and that these peptides have high resistance to enzymatic digestion with proteases in the living body.

TABLE 1

| Amino acid | Residue 1 (pmol) | Residue 2 (pmol) | Residue 3 (pmol) | Residue 4 (pmol) | Content in casein (wt %) |
|---|---|---|---|---|---|
| Asp | 82 | 304 | 115 | 63 | 6.6 |
| Glu | 139 | 127 | 89 | 121 | 20.5 |
| Asn | 55 | 49 | 46 | 91 | incl. in Asp |
| Gln | 80 | 97 | 104 | 80 | incl. in Glu |
| Ser | 105 | 36 | 27 | 16 | 5.23 |
| Thr | 31 | 16 | 25 | 18 | 4.2 |
| His | 28 | 94 | 58 | 0 | 2.6 |
| Gly | 256 | 38 | 33 | 16 | 1.9 |
| Ala | 323 | 101 | 58 | 30 | 2.8 |
| Tyr | 725 | 114 | 52 | 28 | 5.4 |
| Arg | 13 | 7 | 6 | 8 | 3.6 |
| Met | 182 | 43 | 36 | 10 | 2.5 |
| Val | 869 | 127 | 196 | 64 | 6.1 |
| Pro | 42 | 1371 | 431 | 186 | 10.1 |
| Trp | 94 | 46 | 26 | 6 | 1.3 |
| Phe | 800 | 88 | 60 | 28 | 4.6 |
| Lys | 81 | 33 | 57 | 19 | 7.5 |
| Ile | 350 | 37 | 17 | 10 | 5.1 |
| Leu | 400 | 39 | 50 | 10 | 9.4 |
| Total | 4317 | 2767 | 1447 | 387 | 100.0 |

<Determination of Peptides in Enzymatic Hydrolysate>

The powdered enzymatic hydrolysate obtained above was measured for the contents of the di- and tripeptides shown in Table 2 according to a routine method using various chemically synthesized standard peptides. The results are shown in Table 2.

TABLE 2

| Peptide Sequence | Concentration in 10 mg/ml of Powder (µg/ml) |
|---|---|
| Ile-Pro | 16.0 |
| Glu-Pro | 7.1 |
| Arg-Pro | 10.3 |
| Gln-Pro | 34.5 |
| Met-Pro | 18.4 |
| Tyr-Pro | 128.9 |
| Other Xaa-Pro | 299.4 |
| Ser-Pro-Pro | 2.9 |
| Val-Pro-Pro | 29.5 |
| Ile-Pro-Pro | 28.1 |
| Phe-Pro-Pro | 27.2 |
| Other Xaa-Pro-Pro | 28.8 |

The content of the peptides and free amino acids in a solution of the powder in distilled water was 8.15 mg/ml, the peptide content was 4.57 mg/ml, and the content of Xaa-Pro in the peptides was 514.5 µg. It was confirmed that the percentage of Xaa-Pro in the total amount of the peptides and the free amino acids in the powder was 6.3 wt %. Further, the content of Xaa-Pro-Pro in the peptides was 116.5 µg. It was confirmed that the percentage of Xaa-Pro-Pro in the total amount of the peptides and the free amino acids in the powder was 1.4 wt %.

Production Example 2

*Lactobacillus helveticus* CM4 strain (deposited at International Patent Organism Depositary, National Institute of Advanced Industrial Science and Technology, Tsukuba Central 6, 1-1-1 Higashi, Tsukuba-shi, Ibaraki, Japan, under accession number FERM BP-6060 on Aug. 15, 1997) (referred to as CM4 strain hereinbelow) was provided. The CM4 strain has been deposited under the above-mentioned accession number under the Budapest Treaty on the International Recognition of the Deposit of Microorganisms for the Purposes of Patent Procedure, and has already been patented.

A commercially available skim milk was dissolved in distilled water at 9% (w/w) solid content, subjected to high temperature pasteurization in an autoclave at 105° C. for 10 minutes, and cooled to the room temperature. Then the solution was inoculated with 3% (v/w) of a fermentation liquid of CM4 strain starter (cell count $5 \times 10^8$ cells/ml), and fermented under static conditions at 37° C. for 24 hours to obtain a CM4 fermented milk. The CM4 fermented milk thus obtained was pasteurized at 80° C., and lyophilized to obtain a CM4 fermented powder.

Example 1 and Comparative Examples 1-3

The casein enzymatic hydrolysate prepared in Production Example 1 (Example 1), CM4 fermented powder prepared in Production Example 2 (Comparative Example 1), sodium caseinate from cow's milk (Comparative Example 2), and amino acids obtained by acid hydrolysis of casein from cow's milk (Comparative Example 3) were provided as test materials.

On the other hand, a suitable amount of *M. tuberculosis* H37a (manufactured by WAKO PURE CHEMICAL INDUSTRIES, LTD.), which had been killed by heating, was measured out, and made into a fine powder in an agate mortar. Then liquid paraffin (manufactured by WAKO PURE CHEMICAL INDUSTRIES, LTD.) was added in small portions to suspend, thereby preparing a 5 mg/ml suspension, which was used as an adjuvant for sensitization. This adjuvant for sensitization was prepared on the day of sensitization with the adjuvant as will be discussed later.

Female Lewis rats (SPF) of 8 weeks of age were preliminarily bred for 7 days before subjected to the test. Throughout the preliminary breeding period and the test period, the rats were raised in SPF barrier facilities at a room temperature of 24±3° C. and a relative humidity of 55±15%, with the lighting hours of 8:00 to 18:00 and the air exchange rate of 18 times/hour. The rats were housed 2 to 3 per cage, and all the groups were allowed free access to solid feed (trade name MF, manufactured by ORIENTAL YEAST CO., LTD.) and sterilized deionized water. The rats were identified by picric acid applied on the fur.

After the preliminary breeding, 5 groups of rats, 8 animals per group, were individually immobilized on a restraint table under ether anesthesia, and injected with 0.1 ml of the adjuvant for sensitization prepared above through the paw of the right hind leg to induce arthritis. The day of induction was made day 0.

Next, from day 0 today 21, 4 groups of rats were given one of the test materials diluted to 10% with a 0.5% CMC (carboxymethylcellulose) solution once a day at 1 ml/100 g by forced oral administration with a rat feeding needle. As a control, one group of rats were given a 0.5% CMC solution not containing the test material. The animals were observed for the following test items.

Performance status: Symptoms were observed once a day, and recorded on a recording sheet.

Body weight: The body weight was taken on a scale on days 0, 5, 9, 14, 19, and 22.

Arthritis score: Erythema, swelling, and rigidities were visually observed at three sites other than the sensitized right hind leg, i.e., right foreleg, left foreleg, and left hind leg, and scored 0 for none, 1 for slight, 2 for medium, 3 for slightly severe, and 4 for severe symptoms, with the maximum total scores of 12 points. The observations were made on days 0, 5, 9, 14, 19, and 22.

Leg volume: The volume of the right and left hind legs was measured with a foot volume meter (trade name TK-105, manufactured by MUROMACHI KIKAI CO., LTD.). The measurement was made on the same day on which the arthritis score was taken.

The arthritis scores thus taken are indicated as the average of each group±standard error. The statistical significance of the values for each group with respect to those of the control group (1 group) was tested by analysis of variance (ANOVA) using an analysis software (StatView, Abacus Inc., USA), and was confirmed as homoscedastic. The comparison between the groups was made by a multiple comparison test, Fisher's PLSD test. The difference was statistically significant when $p<0.05$.

The arthritis scores are shown in Table 3. Incidentally, no remarkable change in body weight was observed in each group with respect to the control. As to the performance status, none of the groups exhibited abnormal symptoms other than the symptoms of arthritis throughout the test period.

TABLE 3

|  | day 0 | day 5 | day 9 | day 14 | day 19 | day 22 |
| --- | --- | --- | --- | --- | --- | --- |
| Control | 0.00 | 0.00 | 1.00 ± 0.27 | 7.25 ± 0.56 | 10.25 ± 0.41 | 10.38 ± 0.42 |
| Example 1 | 0.00 | 0.00 | 1.00 ± 0.33 | 5.25 ± 0.75 | 8.00 ± 0.82 | 8.50 ± 0.63 |
|  | (NS) | (NS) | (NS) | (p < 0.05) | (p < 0.05) | (p < 0.05) |
| Comp. Ex. 1 | 0.00 | 0.00 | 1.00 ± 0.42 | 7.75 ± 0.86 | 10.25 ± 0.96 | 9.63 ± 0.84 |
|  | (NS) | (NS) | (NS) | (NS) | (NS) | (NS) |
| Comp. Ex. 2 | 0.00 | 0.00 | 1.25 ± 0.37 | 8.25 ± 0.62 | 10.50 ± 0.33 | 10.38 ± 0.32 |
|  | (NS) | (NS) | (NS) | (NS) | (NS) | (NS) |
| Comp. Ex. 3 | 0.00 | 0.00 | 0.88 ± 0.23 | 6.75 ± 0.75 | 10.38 ± 0.46 | 10.13 ± 0.52 |
|  | (NS) | (NS) | (NS) | (NS) | (NS) | (NS) |

The value in ( ) indicates the significance, and NS means no significance.

From the arthritis scores shown in Table 3, it is seen that the increase in score was significantly suppressed (p<0.05) on days 14, 19, and 22 in the group given the test material of Example 1.

Example 2

The casein enzymatic hydrolysate prepared in Production Example 1 (Example 2) as a test material and Ibuprofen (manufactured by WAKO PURE CHEMICAL INDUSTRIES, LTD.) as a positive control were provided.

As in Example 1, the adjuvant for sensitization was prepared on the day of sensitization with the adjuvant as will be discussed later.

Female Lewis rats (SPF) of 8 weeks of age were preliminarily bred for 7 days before subjected to the test. Throughout the preliminary breeding period and the test period, the rats were raised in SPF barrier facilities at a room temperature of 24±3° C. and a relative humidity of 55±15%, with the lighting hours of 7:00 to 19:00 and the air exchange rate of 18 times/hour. The rats were housed 2 to 3 per cage, and all the groups were allowed free access to solid feed (trade name MF, manufactured by ORIENTAL YEAST CO., LTD.) and sterilized deionized water. The rats were identified by picric acid applied on the fur.

After the preliminary breeding, 6 groups of rats, 8 animals per group, were individually immobilized on a restraint table under ether anesthesia, and injected with 0.1 ml of the adjuvant for sensitization prepared above through the paw of the right hind leg to induce arthritis. The day of induction was made day 0.

Next, from day 0 to day 21, 5 groups of rats were given the test material casein enzymatic hydrolysate diluted to 5% (EL 5%), 10% (EL 10%), or 20% (EL 20%), or Ibuprofen diluted to 0.3%, with a 0.5% CMC solution once a day at 1 ml/100 g by forced oral administration with a rat feeding needle. As a control, one group of rats were given a 0.5% CMC solution not containing the test material, and another group of rats were not treated. The animals were observed for the following test items.

Performance status: Symptoms were observed once a day, and recorded on a recording sheet.

Body weight: The body weight was taken on a scale on days 0, 5, 9, 14, 19, and 21.

Arthritis score: Erythema, swelling, and rigidities were visually observed at three sites other than the sensitized right hind leg, i.e., right foreleg, left foreleg, and left hind leg, and scored 0 for none, 1 for slight, 2 for medium, 3 for slightly severe, and 4 for severe symptoms, with the maximum total scores of 12 points. The observations were made on days 0, 5, 9, 14, 19, and 21.

Leg volume: The volume of the right and left hind legs was measured with a foot volume meter (trade name TK-105, manufactured by MUROMACHI KIKAI CO., LTD.). The measurement was made on the same day on which the arthritis score was taken.

Plasma Analysis: On the day after the completion of the test (day 22) and on the following day (day 23), blood was collected transcardially from the rats with a syringe (heparin Na added) under ether inhalation anesthesia, and centrifuged. The resulting supernatant (plasma) was measured for nitric oxide (NO) by the Griess test using $NO_2/NO_3$ Assay Kit-CII Colorimetric (manufactured by DOJINDO LABORATORIES), and for prostaglandin $E_2$ ($PGE_2$) by the EIA test using Prostaglandin $E_2$ EIA Kit-Monoclonal (manufactured by Cayman Chemical Company).

The arthritis scores, leg volume, NO, and $PGE_2$ thus determined are indicated as the average of each group±standard error. The statistical significance of the values for each group with respect to those of the control group (1 group) was tested by analysis of variance (ANOVA) using an analysis software (Stat View, Abacus Inc., USA), and was confirmed as homoscedastic. The comparison between the groups was made by a multiple comparison test, Fischer's PLSD test. The difference was statistically significant when p<0.05.

The arthritis scores are shown in Table 4, the results of measurement of the sensitized leg volume in Table 5, the non-sensitized leg volume in Table 6, the plasma $PGE_2$ in FIG. 1, and the plasma NO in FIG. 2. Incidentally, no remarkable change in body weight was observed in each group with respect to the control. As to the performance status, none of the groups exhibited abnormal symptoms other than the symptoms of arthritis throughout the test period.

TABLE 4

|  | day 0 | day 5 | day 9 | day 14 | day 19 | day 21 |
| --- | --- | --- | --- | --- | --- | --- |
| Non-treated Group 0.5% CMC | 0 (NS) | 0 (NS) | 0 (p < 0.001) | 0 (p < 0.001) | 0 (p < 0.001) | 0 (p < 0.001) |
| Control Group 0.5% CMC | 0 | 0 | 1.5 ± 0.3 | 9.4 ± 0.5 | 11.3 ± 0.4 | 11.5 ± 0.4 |
| EL 5% | 0 (NS) | 0 (NS) | 1.8 ± 0.3 (NS) | 8.1 ± 0.6 (NS) | 11.0 ± 0.3 (NS) | 11.0 ± 0.5 (NS) |
| EL 10% | 0 (NS) | 0 (NS) | 1.3 ± 0.3 (NS) | 8.0 ± 0.7 (NS) | 10.8 ± 0.4 (NS) | 10.6 ± 0.4 (NS) |
| EL 20% | 0 (NS) | 0 (NS) | 0.4 ± 0.2 (p < 0.01) | 6.0 ± 1.0 (p < 0.05) | 8.8 ± 0.8 (p < 0.01) | 9.0 ± 0.9 (p < 0.05) |
| Ibuprofen 0.3% | 0 (NS) | 0 (NS) | 0.1 ± 0.1 (p < 0.01) | 6.5 ± 0.6 (p < 0.01) | 9.0 ± 0.5 (p < 0.01) | 9.5 ± 0.3 (p < 0.01) |

The value in ( ) indicates the significance, and NS means no significance.

TABLE 5

|  | day 0 | day 5 | day 9 | day 14 | day 19 | day 21 |
|---|---|---|---|---|---|---|
| Non-treated Group 0.5% CMC | 1.36 ± 0.01 (NS) | 1.37 ± 0.01 (p < 0.001) | 1.35 ± 0.01 (p < 0.001) | 1.36 ± 0.00 (p < 0.001) | 1.37 ± 0.01 (p < 0.001) | 1.36 ± 0.01 (p < 0.001) |
| Control Group 0.5% CMC | 1.36 ± 0.00 | 3.14 ± 0.03 | 3.22 ± 0.05 | 3.73 ± 0.09 | 3.86 ± 0.10 | 3.84 ± 0.09 |
| EL 5% | 1.35 ± 0.01 (NS) | 3.01 ± 0.06 (NS) | 3.04 ± 0.06 (p < 0.05) | 3.50 ± 0.09 (NS) | 3.62 ± 0.07 (p < 0.05) | 3.56 ± 0.09 (p < 0.05) |
| EL 10% | 1.34 ± 0.01 (NS) | 2.98 ± 0.05 (NS) | 3.07 ± 0.09 (NS) | 3.79 ± 0.08 (NS) | 3.78 ± 0.12 (NS) | 3.74 ± 0.08 (NS) |
| EL 20% | 1.37 ± 0.01 (p < 0.05) | 2.92 ± 0.05 (p < 0.01) | 2.83 ± 0.05 (p < 0.001) | 3.52 ± 0.10 (NS) | 3.58 ± 0.07 (p < 0.05) | 3.44 ± 0.11 (p < 0.01) |
| Ibuprofen 0.3% | 1.36 ± 0.004 (NS) | 2.69 ± 0.06 (NS) | 2.70 ± 0.06 (p < 0.001) | 3.26 ± 0.08 (p < 0.001) | 3.00 ± 0.08 (p < 0.001) | 2.72 ± 0.09 (p < 0.001) |

The value in ( ) indicates the significance, and NS means no significance.

TABLE 6

|  | day 0 | day 5 | day 9 | day 14 | day 19 | day 21 |
|---|---|---|---|---|---|---|
| Non-treated Group 0.5% CMC | 1.35 ± 0.005 (NS) | 1.36 ± 0.009 (NS) | 1.35 ± 0.007 (p < 0.001) | 1.36 ± 0.007 (p < 0.001) | 1.36 ± 0.006 (p < 0.001) | 1.37 ± 0.006 (p < 0.001) |
| Control Group 0.5% CMC | 1.36 ± 0.01 | 1.37 ± 0.01 | 1.73 ± 0.09 | 3.16 ± 0.07 | 3.14 ± 0.08 | 3.17 ± 0.04 |
| EL 5% | 1.36 ± 0.01 (NS) | 1.36 ± 0.01 (NS) | 1.79 ± 0.09 (NS) | 2.83 ± 0.10 (NS) | 2.99 ± 0.05 (NS) | 3.03 ± 0.06 (NS) |
| EL 10% | 1.36 ± 0.01 (NS) | 1.35 ± 0.01 (NS) | 1.56 ± 0.06 (p < 0.05) | 2.85 ± 0.10 (p < 0.05) | 2.92 ± 0.12 (p < 0.05) | 2.78 ± 0.06 (p < 0.05) |
| EL 20% | 1.36 ± 0.01 (NS) | 1.36 ± 0.01 (NS) | 1.39 ± 0.01 (p < 0.01) | 2.54 ± 0.17 (p < 0.001) | 2.58 ± 0.11 (p < 0.001) | 2.58 ± 0.10 (p < 0.001) |
| Ibuprofen 0.3% | 1.36 ± 0.01 (NS) | 1.37 ± 0.01 (NS) | 1.38 ± 0.01 (p < 0.001) | 2.26 ± 0.06 (p < 0.001) | 2.43 ± 0.06 (p < 0.001) | 2.23 ± 0.03 (p < 0.001) |

The value in ( ) indicates the significance, and NS means no significance.

From the arthritis scores shown in Table 4, it is seen that the increase in score was significantly suppressed (p<0.01) on days 9, 14, 19, and 21 in the group given 2000 mg/kg of the test material of Example 2.

From the results of the measurement of the sensitized leg volume shown in Table 5, it is seen that the increase in sensitized leg volume was significantly suppressed (p<0.05) on days 9, 19, and 21 in the group given 500 mg/kg of the test material of Example 2, and was also significantly suppressed (p<0.001) on days 5, 9, 19, and 21 in the group given 2000 mg/kg of the test material of Example 2.

From the results of the measurement of the non-sensitized leg volume shown in Table 6, it is seen that the increase in non-sensitized left hind leg volume was significantly suppressed (p<0.001) on days 9, 14, 19, and 21 in the group given 1000 mg/kg or 2000 mg/kg of the test material of Example 2.

From the results of the plasma $PGE_2$ shown in FIG. 1, it is seen that the increase in plasma $PGE_2$ level was significantly suppressed (p<0.05) in the group given 2000 mg/kg of the test material of Example 2.

From the results of the measurement of NO shown in FIG. 2, it is seen that the increase in plasma NO ($NO_2^- + NO_3^-$) level was significantly suppressed (p<0.05) in the group given 500, 1000, or 2000 mg/kg of the test material of Example 2.

Incidentally, the adjuvant arthritis model test described above is widely recognized as a model of chronic rheumatoid arthritis as described, for example, in *Ensho* (Inflammation) Vol. 15, No. 5 (1995), p 395-399 (Journal of *Nihon Ensho Gakkai* (The Japanese Society of Inflammation)).

What is claimed is:

1. A method for treating rheumatoid arthritis comprising orally administering to a subject in need thereof an effective amount of casein hydrolysate comprising free amino acids and peptides obtained by hydrolyzing animal milk casein to have an average chain length of not longer than 2.1 in terms of the number of amino acid residues, or a mixture of free amino acids and peptides contained in said hydrolysate.

2. The method according to claim 1, wherein said casein hydrolysate is a product of enzymatic digestion of animal milk casein with an enzyme derived from *Aspergillus*.

3. The method according to claim 1, wherein said effective amount is 0.04 to 100 g per day in terms of dried casein hydrolysate or dried peptide and free amino acids contained in the casein hydrolysate.

4. The method according to claim 1, wherein said effective amount is administered in several divided doses per day.

5. The method according to claim 1, wherein said effective amount is administered regularly.

6. The method according to claim 1, wherein said peptides comprise peptides resistant to in vivo digestion consisting of dipeptides of the sequence Xaa-Pro and tripeptides of the sequence Xaa-Pro-Pro, a content of said dipeptides having the sequence Xaa-Pro in the casein hydrolysate is not lower than 5 wt % and a content of said tripeptides having the sequence Xaa-Pro-Pro in the casein hydrolysate is not lower than 1 wt %, of the total amount of the peptides and the free amino acids in the hydrolysate, with Xaa being any amino acid.

* * * * *